United States Patent [19]
Klostermeyer et al.

[11] Patent Number: 5,891,195
[45] Date of Patent: Apr. 6, 1999

[54] COMBINED PROSTHETIC AORTIC HEART VALVE AND VASCULAR GRAFT WITH SEALED SEWING RING

[75] Inventors: Tammi E. Klostermeyer; Joseph A. Sauter; Louis A. Campbell, all of Austin, Tex.

[73] Assignee: Sulzer Carbomedics Inc., Austin, Tex.

[21] Appl. No.: 652,953

[22] Filed: May 24, 1996

[51] Int. Cl.$^6$ ........................................... A61F 2/24
[52] U.S. Cl. ........................................................ 623/2
[58] Field of Search ........................... 623/2, 900

[56] References Cited

U.S. PATENT DOCUMENTS

| | | | |
|---|---|---|---|
| 3,130,419 | 4/1964 | Edwards | 623/2 |
| 3,725,961 | 4/1973 | Magovern et al. | 623/2 |
| 4,666,442 | 5/1987 | Arru et al. | 623/2 |
| 4,680,031 | 7/1987 | Alonso | 623/2 |
| 5,035,709 | 7/1991 | Wieting et al. | 623/2 |
| 5,123,919 | 6/1992 | Sauter et al. | 623/2 |
| 5,776,185 | 7/1998 | Verona et al. | 623/2 |

OTHER PUBLICATIONS

Bentall and DeBono, "A Technique for Complete Replacement of the Ascending Aorta", *Thorax*, 1968, V.23, pp. 338–339.

Copeland et al. "New Technique for Improving Hemostasis in Aortic Root Replacement with Composite Graft", Ann Thorac. Surg. 1993; 55: 1027–9.

Advertisement, Johnson & Johnson, "Proximal Aortic Dissection—Anastomotic Leakage'" 1995.

*Primary Examiner*—David H. Willse
*Attorney, Agent, or Firm*—Kenneth S. Barrow

[57] ABSTRACT

A combined heart valve and vascular graft, or "valve/graft combination", wherein the heart valve has a sewing ring that is substantially impervious to blood flow. In our preferred embodiment, the sewing ring comprises a solid circular silicone insert which supports the sewing ring radially outwardly form the valve and forms a shield to prevent the flow of blood through the sewing ring.

8 Claims, 2 Drawing Sheets

COMBINED PROSTHETIC AORTIC HEART VALVE AND VASCULAR GRAFT WITH SEALED SEWING RING

BACKGROUND OF OUR INVENTION

Our invention relates to prosthetic heart valves, and in particular to prosthetic heart valves which are combined with an integral vascular graft for use in replacing a diseased aortic valve and a portion of the aorta of a patient.

Prosthetic heart valves replace diseased valves in a human heart. These valves fall generally into two categories. Biologic valves are comprised of leaflets made of a flexible biologic material. Depending on the source of the leaflet material, the valve may be either a xenograft, that is, harvested from a non-human cadaver, or an allograft, that is, harvested from a human cadaver. The second major category of prosthetic heart valves is mechanical valves. These valves usually comprise an annular body supporting one, two or three leaflets of a non-biologic material. The annular body and leaflets are frequently formed in pyrolytic carbon, a particularly hard and wear resistant form of carbon. The annular body is captured within a sewing ring so that the valve may be attached to heart tissue at the location of the replaced valve. Mechanical valves with flexible, polymeric leaflets are also known.

Functioning valves are critical to the proper action of the heart. If a valve becomes diseased, it may be replaced by a prosthetic valve. If degeneration of a valve has occurred, however, it is likely that surrounding blood vessels are also diseased. Particularly in the case of the aortic valve, surgeons have found that not only the valve but also the adjacent aorta degenerate. Consequently, both valve and a segment of the ascending aorta may be replaced at the same time. In 1968 Bentall and DeBono described a method for attaching a commercially available graft to a Starr-Edwards mechanical heart valve for the complete replacement of an aneurysmal aorta and aortic valve. See, "A Technique for Complete Replacement of the Ascending Aorta", *Thorax*, 1968; V. 23, pgs. 338–339. After implanting the mechanical heart valve, a surgeon would stitch a segment of vascular graft to the sewing ring of the mechanical valve. The juncture between the valve and the graft was abrupt and there was usually a sharp change of diameter to be expected between the valve and the graft.

Subsequently, Shiley Corp., in conjunction with cardiovascular surgeons, produced a composite valve and pre-attached graft. Between the valve and the graft, there was a relatively long, tapered fabric section. It was suggested that the taper would provide a smooth transition between the valve and the graft to reduce turbulent flow. Tapered sections of 8 to 12 millimeters have been widely used by Shiley and others offering composite valve/graft combinations.

Combined mechanical heart valves and vascular grafts having a shortened transition area between the valve and the graft are also known. One such combination is disclosed in U.S. Pat. No. 5,123,919. The mechanical valve comprises a rigid circular annular body supporting internal leaflets, a stiffening ring surrounding the annular body, and a sewing ring for attaching the valve to the heart. The stiffening ring also captures a proximal end of the vascular graft between the stiffening ring and the annular body.

From 1968 until 1991, clean, sterile polyester grafts were generally used for combined mechanical heart valves and grafts. In some cases, extremely low porosity grafts were used to minimize leakage, which was reduced to about 50 to 100 cc/min/cm$^2$. These low porosity grafts were initially successful in minimizing patient blood loss, but they suffered from a long-term failure mode. In use, a neo-intimal layer can build up on the interior surface of the graft where it is constantly exposed to blood flow. Eventually, the neo-intimal layer may become so thick that the shear stress from the flowing blood may peel it off the inside of the smooth, low porosity graft, resulting in a large solid embolism that could cause significant injury to the patient. To avoid this problem, higher porosity grafts, with leak rates in excess of 200 cc/min/cm$^2$, were employed. These higher porosity grafts allow the neo-intimal layer to grow into the interstices of the graft, creating a mechanical bond that has successfully decreased the problem of neo-intimal layer peeling. Blood loss with higher porosity grafts was minimized by pre-clotting the graft prior to implantation. Typically, the graft was dipped into the patient's own blood. Then the whole assembly was heated for several minutes to dry the blood, producing a semi-impervious coating. Even with this pre-clotting operation, significant blood loss was common. In an effort to decrease this blood loss, the remnant of aortic tissue was frequently wrapped around the graft. This resulted, however, in the formation of a hematoma, capturing blood between the outside of the graft and the inside of the aortic remnant. Professor Cabrol developed a technique of attaching a small (8–10 mm) graft from the site of this hematoma to the right atrium to relieve the interior pressure before the hematoma burst with fatal consequences. Unfortunately, this small graft frequently occluded, so this practice fell out of favor as sealed grafts and fibrin glue came into use.

A pre-clotting procedure adds about 30 minutes to an operation, during which time the patient is subjected to artificial circulation and its associated risks. In some cases surgeons would pre-clot the graft with fibrin glue to avoid this delay. This glue is expensive and has not been widely available in highly regulated jurisdictions because of the risk of disease transmission associated with this human blood product. In 1991, combined mechanical heart valves and vascular grafts became available with pre-sealed, medium porosity grafts. These devices employed collagen or gelatine sealed grafts. This sealing technology prevented significant blood loss through the graft at the time of surgery. After blood flow is re-established, the sealing material dissolves or is digested, leaving a graft with sufficient porosity to eliminate neo-intimal peel.

Aortic heart valves alone are usually implanted within walls of the cardiovascular system at the aortic annulus. Any blood leaking around the heart valve, for example, either past or through the sewing ring of the valve, would nevertheless still be inside the cardiovascular system. Blood would not be leaking into the body cavity as the left ventricle forces blood into the body. Vascular grafts, since they replace a portion of the aorta, have been designed to resist a pressure difference and prevent blood from leaking through the graft into the body cavity. Aortic heart valve and vascular graft combinations, however, have not adequately addressed the problem of blood leakage through and around the sewing ring of the heart valve.

It is a principle object of our invention, therefore, to provide a cardiac valve and vascular graft combination which resists blood leakage around or through the sewing ring of the heart valve.

Another object of our invention is to provide a valve/graft combination with a relatively impervious sewing ring.

Another object of our invention is to provide a sewing ring in a heart valve/graft combination with a solid silicone baffle.

These and other objects and features of our invention will be apparent from the following description taken with reference to the accompanying drawings.

SUMMARY OF OUR INVENTION

We have invented a combined heart valve and vascular graft, or "valve/graft combination", wherein the heart valve has a sewing ring that is substantially impervious to blood flow. In our preferred embodiment, the sewing ring comprises a solid circular silicone washer or insert which supports the sewing ring radially outwardly from the valve and forms a shield to prevent the flow of blood through the sewing ring.

DETAILED DESCRIPTION OF OUR PREFERRED EMBODIMENT

We will now describe our preferred embodiment, with reference to the accompanying figures. Like numerals are used to designate like parts throughout.

Figure 1:
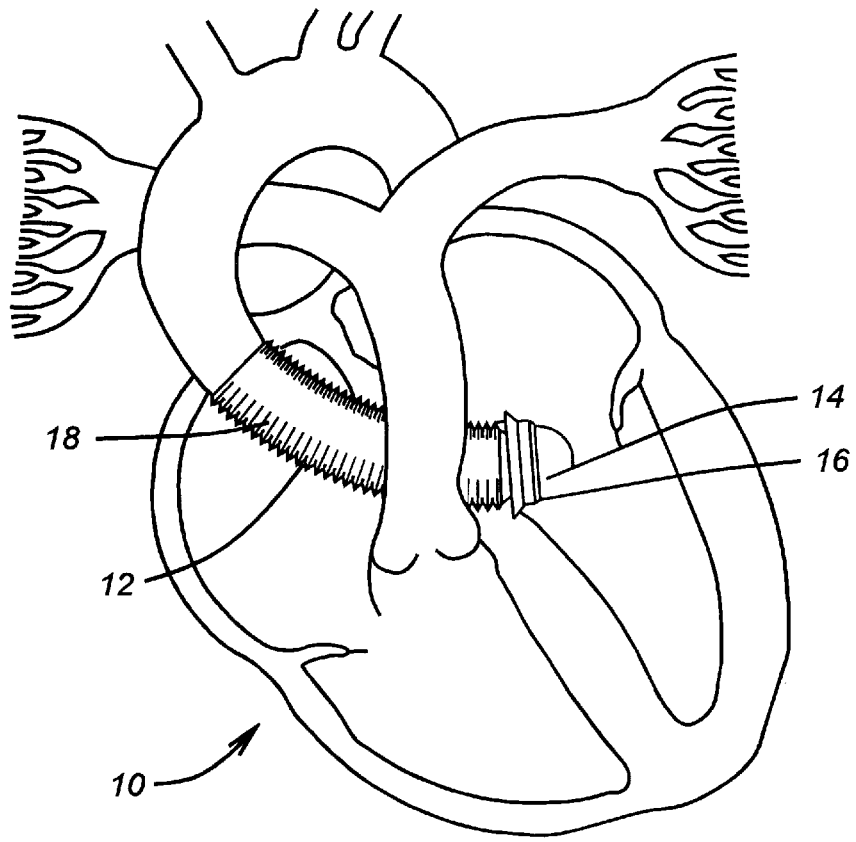
FIG. 1 is a cross-sectional view of a human heart, showing a combined mechanical heart valve and vascular graft according to our invention.

FIG. 1 illustrates a cross-sectional view of a human heart 10 with a combined mechanical heart valve and graft 12 according to our invention. The combined valve and graft 12 is shown replacing an aortic valve and a portion of the ascending aorta. The combined valve and graft comprises a mechanical heart valve 14 with a surrounding sewing ring 16. Immediately adjacent the sewing ring 16 there is a vascular graft 18. With the illustrated stiffening ring design, the internal diameter of the valve can be relatively large. Since the taper is very short, the ostia of the coronary arteries can be reattached to the graft 18 immediately adjacent the valve.

Figure 2:
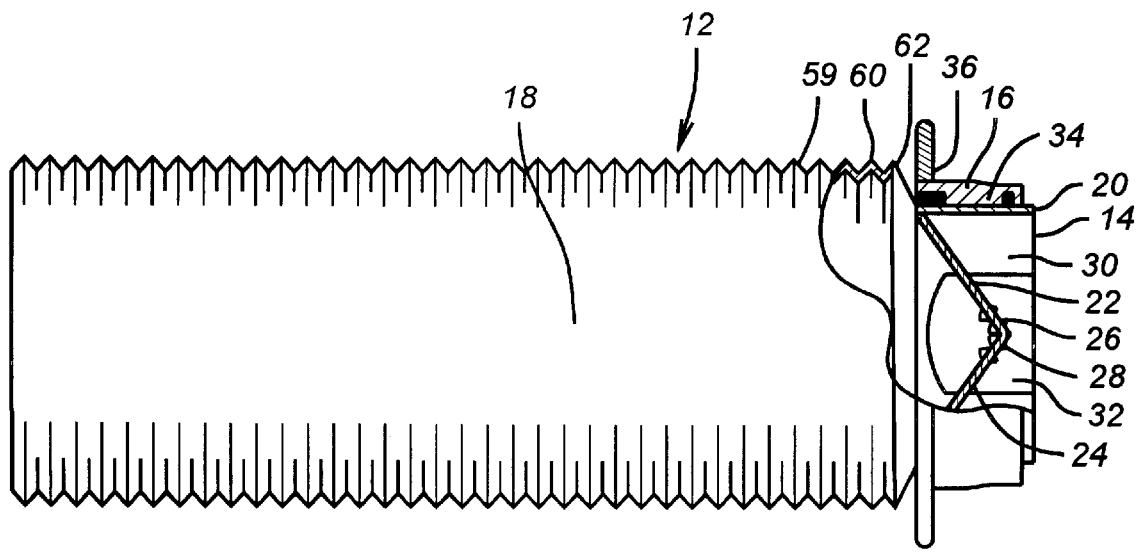
FIG. 2 is a plan view with partial cutaway section of a combined heart valve and graft according to our invention.
Figure 4:
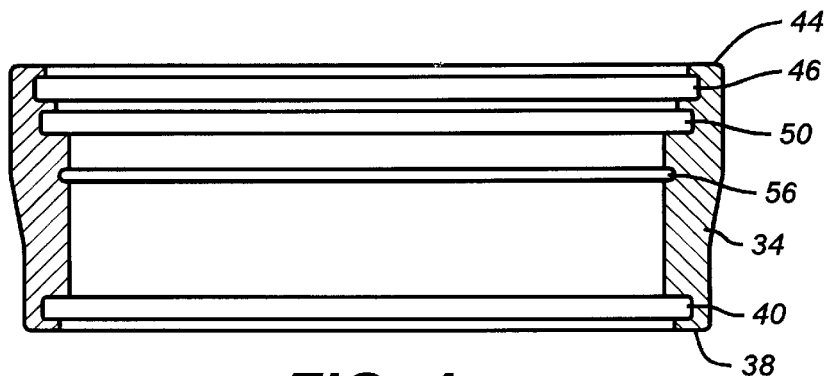
FIG. 4 is a cross-sectional plane view of a stiffening ring.

The structure of the combined valve and graft can be more clearly seen in FIG. 2. The mechanical valve 14 comprises an annular body 20 forming an orifice containing leaflets 22, 24. The leaflets 22, 24 swing about pivots 26, 28. We have illustrated a bileaflet mechanical valve. In such valves, there would be two pivots for each leaflet, each pivot diametrically opposed to another across the annular body 20. Of course, a mechanical valve having one, or three, or more leaflets or a biological valve could also be used without departing from the spirit or teachings of our invention. On an interior side 30 of the annular body 20, adjacent the pivots 26, 28, a flattened area 32 provides a region on the annular body to support the leaflets as they pivot between open and closed positions. As is known in this art, additional conventional features may be provided, such as stops to limit the rotational motion of the leaflets.

Figure 3:
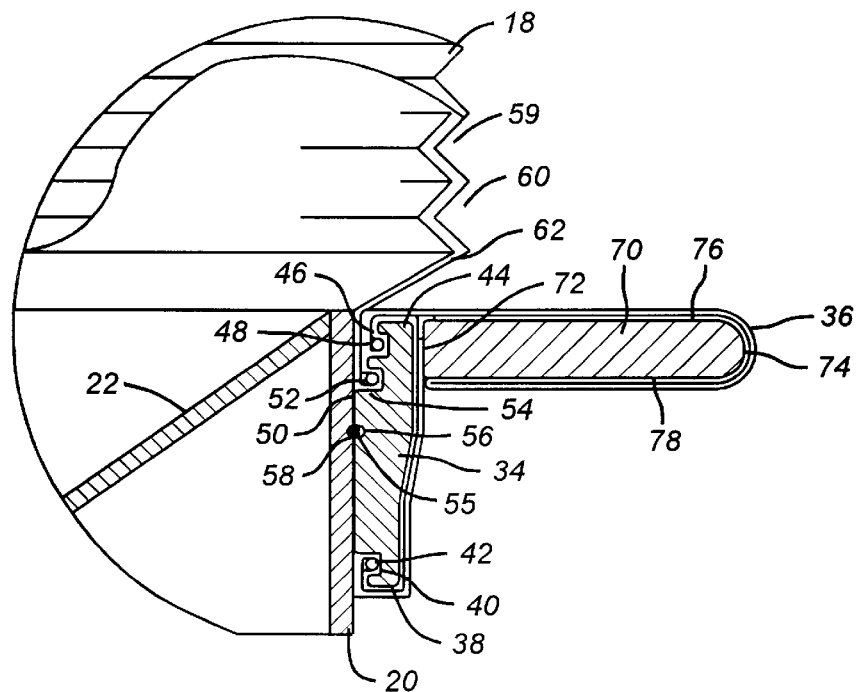
FIG. 3 is an enlarged view of a portion of the combined valve and graft of FIG. 2.
Figure 5:
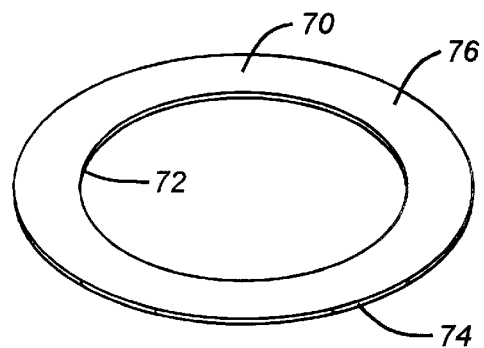
FIG. 5 is a prospective view of a silicone washer for use in the sewing ring of the valve/graft combination.

Surrounding the annular body 20, the sewing ring 16 comprises a stiffening ring 34. The annular body and leaflets are preferably formed of pyrolytic carbon which is hard and wear-resistant, but somewhat brittle. The stiffening ring 34 is usually metal, for example, cobalt-chromium or titanium alloys. A fabric sewing collar 36 is captured between the annular body 20 and the stiffening ring 34. The fabric collar 36 comprises multiple folds of cloth, as illustrated in FIG. 3. At an upstream edge 38 of the stiffening ring 34, we have made a circumferential groove 40. A fold in the fabric collar 36 is captured within this groove with a metal ring 42. Similarly, at a downstream edge 44 of the stiffening ring 34, we have made a second groove 46 which captures another fold of the fabric collar 36 with a second ring 48. Immediately adjacent the downstream grove 46 we have made a third groove 50. The third groove 50 captures the vascular graft 18 between the stiffening ring 34 and the annular body 20, thus providing a sharp, non-stitched transition between the heart valve and the graft. A third circumferential ring 52 is placed within the third groove 50 to capture a proximal end 54 of the graft. As seen in FIG. 3, the vascular graft 18 passes between the annular body 20 and the combined stiffening ring 34 and fabric collar 36. The fabric collar 36 surrounds a flat, wide silicone washer 70. As seen in FIG. 3 and FIG. 5, the washer 70 has a circular inner edge 72 which will fit tightly around the stiffening ring 34. An outer edge 74 spaced radially outwardly from the inner edge defines a relatively wide area so that a seal can be formed between the sewing ring and the aortic annulus when the combination 12 is implanted. The washer 70 has an upper surface 76 between the edges 72, 74 and a parallel lower surface 78 spaced away therefrom. The washer 70 has no perforations and is substantially impervious to blood. An impervious washer might also be formed of silicone impregnated cloth or other suitable material.

The annular body and leaflets are held within the sewing ring 16 by an interference ring 55 which rests in opposed grooves 56, 58 in the stiffening ring and the annular body respectively. Alternative structures for connecting an annular body and stiffening ring are shown in our U.S. Pat. No. 5,071,431 assigned to Carbomedics, Inc.

The vascular graft 18 comprises a tubular fabric structure having corrugated walls 59. At a proximal end 60, adjacent the heart valve 14, a short taper 62 is provided. This taper is formed by removing small, triangular sections and sewing the resulting edges together. Usually, four such sewn features spaced around the proximal end are needed.

The tapered section 62 is extremely short and the sewn edges do not extend into a region where the coronary arteries would be attached. Preferably, the taper should measure 4 mm or less in an axial direction and preferably 2 mm or less. The ostia of the coronary arteries, therefore, can be attached into the graft 18 immediately downstream from the mechanical valve 14. Moreover, the diameter of the graft 18 at the point of attachment of the coronary arteries is relatively large. This permits the arteries to be attached without stretching.

Our invention may be embodied in other specific forms without departing from the spirit or essential characteristics thereof. Our invention therefore, is to be defined by the appended claims, and not by the foregoing description. All variations which come within the meaning and doctrine of equivalency of claims, are therefore intended to be included therein.

We claim as our invention:

1. An implantable prosthetic device comprising
    a prosthetic heart valve having
        an orifice,
        at least one leaflet mounted within said orifice, movable between open and closed positions, and
        a sewing ring surrounding said orifice, said sewing ring having means for substantially preventing blood from passing through said sewing ring, and a vascular graft having a proximal end and a distal end, the proximal end being connected to said prosthetic heart valve.

2. The implantable prosthetic device according to claim 1 wherein the sewing ring further comprises an insert circumferentially disposed around said orifice.

3. The implantable prosthetic device according to claim 2 wherein said insert is comprised of an impervious material.

4. The implantable prosthetic device according to claim 3 wherein said insert is comprised of silicone.

5. The implantable prosthetic device according to claim 1 wherein said sewing ring further comprises a stiffening ring and a fabric collar, said fabric collar being captured between said stiffening ring and said orifice.

6. The implantable prosthetic device according to claim 5 wherein the sewing ring further comprises a insert circumferentially disposed around said stiffening ring.

7. The implantable prosthetic device according to claim 6 wherein said insert is comprised of an impervious sheet.

8. The implantable prosthetic device according to claim 7 wherein said insert is comprised of silicone.

* * * * *